US011730950B2

(12) United States Patent
Spaniol et al.

(10) Patent No.: US 11,730,950 B2
(45) Date of Patent: Aug. 22, 2023

(54) FORMING PROCESS USING AN OUTER SACRIFICIAL LAYER

(71) Applicant: Heraeus Deutschland GmbH & Co. KG, Hanau (DE)

(72) Inventors: Bernd Spaniol, Hanau (DE); Tim Esposto, Hanau (DE); Andre Weigand, Hanau (DE); Markus Jung, Hanau (DE)

(73) Assignee: Heraeus Deutschland GmbH & Co. KG, Hanau (DE)

( * ) Notice: Subject to any disclaimer, the term of this patent is extended or adjusted under 35 U.S.C. 154(b) by 37 days.

(21) Appl. No.: 17/444,420

(22) Filed: Aug. 4, 2021

(65) Prior Publication Data

US 2022/0040744 A1 Feb. 10, 2022

(30) Foreign Application Priority Data

Aug. 4, 2020 (EP) .................................. 20189385
May 17, 2021 (EP) .................................. 21174186

(51) Int. Cl.
*B21C 1/00* (2006.01)
*B21C 37/06* (2006.01)
*B21C 37/15* (2006.01)
*A61N 1/05* (2006.01)
*A61N 1/36* (2006.01)

(52) U.S. Cl.
CPC ............ *A61N 1/05* (2013.01); *A61N 1/36125* (2013.01); *B21C 1/003* (2013.01); *B21C 37/065* (2013.01); *B21C 37/154* (2013.01); *A61B 2562/125* (2013.01)

(58) Field of Classification Search
CPC ...... A61N 1/05; A61N 1/36125; B21C 1/003; B21C 37/065; B21C 37/154; A61B 2562/125
See application file for complete search history.

(56) References Cited

U.S. PATENT DOCUMENTS

| 3,267,564 | A | * | 8/1966 | Keyes | ........................ B21C 1/22 |
| | | | | | D25/120 |
| 8,845,713 | B2 | * | 9/2014 | Marton | .................... A61L 27/06 |
| | | | | | 623/1.13 |
| 10,529,815 | B2 | * | 1/2020 | Ando | ..................... H01L 29/401 |
| 10,933,233 | B2 | | 3/2021 | Leitold et al. | |
| 2005/0131521 | A1 | * | 6/2005 | Marton | ..................... A61F 2/90 |
| | | | | | 623/1.13 |
| 2008/0255647 | A1 | | 10/2008 | Jensen et al. | |
| 2012/0046721 | A1 | | 2/2012 | Koop | |

(Continued)

FOREIGN PATENT DOCUMENTS

EP 3530314 8/2019
WO 2020/092652 5/2020

*Primary Examiner* — Lawrence Averick
(74) *Attorney, Agent, or Firm* — Dicke, Billig & Czaja, PLLC (57) ABSTRACT

One aspect relates to a process for preparing a shaped metal product, wherein a monolithic metal precursor surrounded by a sacrificial outer element is formed to smaller dimensions, and the sacrificial material is subsequently removed. One aspect further provides a composite for preparing a shaped metal product, and a shaped metal product. Such shaped metal products can be used to manufacture an active implantable medical device or sensor.

13 Claims, 6 Drawing Sheets

(56) References Cited

U.S. PATENT DOCUMENTS

| | | |
|---|---|---|
| 2014/0277322 A1 | 9/2014 | Victorine et al. |
| 2015/0021817 A1 | 1/2015 | Romero et al. |
| 2016/0166801 A1 | 6/2016 | Birdsall et al. |
| 2016/0209127 A1* | 7/2016 | Goto ................... B23P 15/26 |
| 2017/0143220 A1 | 5/2017 | Doerge et al. |
| 2019/0131418 A1* | 5/2019 | Ando ................ H01L 29/42372 |
| 2019/0255317 A1 | 8/2019 | Leitold et al. |
| 2020/0009372 A1 | 1/2020 | Mercanzini et al. |
| 2021/0370053 A1 | 12/2021 | Jin et al. |

* cited by examiner

FORMING PROCESS USING AN OUTER SACRIFICIAL LAYER

CROSS-REFERENCE TO RELATED APPLICATION

This Utility patent application claims priority to European Application No. 21174186.3 filed on May 17, 2021 and European Application No. 20189385.6 filed on Aug. 4, 2020, both of which are incorporated herein by reference.

TECHNICAL FIELD

One aspect relates to a process for preparing a shaped metal product, in particular a medical product, such as a ring electrode or segmented electrode, to a composite for preparing such shaped metal product, and to a resulting shaped metal product. The shaped metal product, or part thereof, is in one embodiment suitable for use in a medical device, in one embodiment an active implantable medical device, but can also be used for other purposes. Examples include medical ring electrodes and segmented electrodes for electrical stimulation or sensing (signal acquisition).

BACKGROUND

Electrodes or electrode parts for medical devices, and in active implantable medical devices, typically have very small dimensions, and the trend in this technical field is towards further miniaturization.

Conventionally, medical electrodes or electrode parts require very expensive and complex manufacturing equipment and processes with many individual work steps. For example, ring electrodes are often manufactured from a rod material by machining such as turning and the excess material inside the ring is removed, for example by spark erosion. Such conventional preparation processes are costly, and can be limited with regard to the shape of the electrode or the part thereof and in terms of the degree of miniaturization which can be achieved.

In EP 3 530 314 A1, a process for preparing a ring electrode is described including providing an outer element, including an outer tube, providing a first inner element, including a first inner tube having a first core of a sacrificial material, providing a second inner element, including a second core of a sacrificial material, forming a composite tube by arranging the first inner element and the second inner element inside the outer element, the first inner element and the second inner element being arranged off-center with respect to one another, drawing the composite tube in a longitudinal direction of the composite tube, separating a composite tube disk from the composite tube, removing the sacrificial material of the first core, and removing the sacrificial material of the second core. However, using different types of tube components as starting materials, there is always a limitation with respect to the geometry, dimensions and/or shape of the final ring electrode. For example, the geometry of the final ring electrode may be governed by the wall thickness of the tube components. Furthermore, the outer shape of the formed tube components are limited to a circular outer shape.

A process for preparing a shaped metal product, such as a ring electrode or a part thereof, is desirable, wherein the process allows for preparing shaped metal products with a higher flexibility and less limitations in terms of the dimensions, geometry and/or shape of product.

For these and other reasons there is a need for the present embodiments.

In view of the foregoing, one embodiment is directed to the provision of an improved, or at least alternative, process for preparing a shaped metal product, such as a medical device or a part thereof. In particular, one embodiment is directed to the provision of a process for preparing a shaped metal product, such as a medical device or a part thereof, which provides a higher flexibility and/or less limitations in terms of dimensions, geometry and/or shape of the ring electrode or a part thereof. The process of one embodiment can be particularly useful in the manufacturing of implantable medical devices for electrical stimulation and sensing.

SUMMARY

Exemplary embodiments are described in the following variants.

A first ($1^{st}$) variant of one embodiment is a process for preparing a shaped metal product, in one embodiment for a medical device, wherein the process includes the steps of:
1) providing a sacrificial outer element including a cavity A;
2) providing a monolithic metal precursor including a cavity B;
3) providing a sacrificial core element;
4) preparing a composite precursor by inserting the monolithic metal precursor into cavity A of the sacrificial outer element, and by inserting the sacrificial core element into cavity B of the monolithic metal precursor;
5) forming the composite precursor obtained in step 4) to obtain a formed composite having a smaller outer diameter than the diameter of the composite precursor obtained in step 4);
6) separating a composite disk from the formed composite obtained in step 5);
7) removing the sacrificial outer element and the sacrificial core element from the composite disk obtained in step 6).

In another variant of the process, the outer shape of the monolithic metal precursor, as seen in a radial cross section, has an open or a closed outer shape. This variant is a $2^{nd}$ variant of one embodiment, that in one embodiment depends on the $1^{st}$ variant one embodiment.

In another variant of the process, the closed outer shape is a shape selected from the list consisting of oval, polygonal, cubic, rectangular, and circular. This variant is a $3^{rd}$ variant of one embodiment, that in one embodiment depends on the $1^{st}$ or $2^{nd}$ variant of one embodiment.

In another variant of the process, the metal precursor includes a tube including the cavity B. This preferred variant is a $4^{th}$ variant of one embodiment, that in one embodiment depends on any of the $1^{st}$ to $3^{rd}$ variants of one embodiment.

In another variant of the process, the open outer shape is a shape selected from the list consisting of U-shaped, L-shaped, S-shaped or H-shaped. This preferred variant is a $5^{th}$ variant of one embodiment, that in one embodiment depends on the 2nd variant of one embodiment.

In another variant of the process, the inner shape of the monolithic metal precursor, as seen in a radial cross section, is a non-circular shape. This preferred variant is a $6^{th}$ variant of one embodiment, that in one embodiment depends on any of the $1^{st}$ to $5^{th}$ variants of one embodiment.

In another variant of the process, the sacrificial outer element and the sacrificial core element are contiguous. This preferred variant is a $7^{th}$ variant of one embodiment, that in one embodiment depends on any of the $1^{st}$ to $6^{th}$ variants of one embodiment.

In another variant of the process, the monolithic metal precursor is prepared by at least one process selected from the group of electrical discharging machining, additive manufacturing, deep-hole drilling and milling. This preferred variant is an $8^{th}$ variant of one embodiment, that in one embodiment depends on any of the $1^{st}$ to $7^{th}$ variants of one embodiment.

In another variant of the process, the monolithic metal precursor includes a metal selected from the group consisting of platinum, gold, iridium, steel, titanium, hafnium, niobium, tantalum, cobalt, nickel, chromium, zirconium, rhenium, tungsten, molybdenum, and alloys of any one of these metals, in one embodiment selected from the group consisting of nickel cobalt alloy, steel, platinum and platinum iridium alloy, and in one embodiment is a platinum iridium alloy. This preferred variant is a $9^{th}$ variant of one embodiment, that in one embodiment depends on any of the $1^{st}$ to $8^{th}$ variants of one embodiment.

In another variant of the process, the sacrificial outer element and/or the sacrificial core element include(s) a non-noble metal or non-noble metal alloy, in one embodiment selected from the group of nickel, copper, steel, and alloys of any one of these metals. This preferred variant is a $10^{th}$ variant of one embodiment, that in one embodiment depends on any of the $1^{st}$ to $9^{th}$ variants of one embodiment.

In another variant of the process, the sacrificial outer element and the sacrificial core element include a metal, and wherein the metal of the monolithic metal precursor has a higher standard electrode potential than the metal of the sacrificial outer element and the sacrificial core element. This preferred variant is a $11^{th}$ variant of one embodiment, that in one embodiment depends on any of the $1^{st}$ to $10^{th}$ variants of one embodiment.

In another variant of the process, step 5) includes a drawing process. This preferred variant is a $12^{th}$ variant of one embodiment, that in one embodiment depends on any of the $1^{st}$ to $11^{th}$ variants of one embodiment.

In another variant the drawing process is carried out with a deformation factor of between 5 and 40%, in one embodiment between 10 and 30%, per individual drawing. This preferred variant is a $13^{th}$ variant of one embodiment, that in one embodiment depends on the $12^{th}$ variant of one embodiment.

In another variant the drawing process is carried out with a die cast having a total included angle $2\alpha$ in the range of from 5 to 20°, in one embodiment from 5 to 15°. This preferred variant is a $14^{th}$ variant of one embodiment, that in one embodiment depends on any of the $12^{th}$ or $13^{th}$ variants of one embodiment.

In another variant of the process, the composite precursor is annealed between individual drawing steps of the drawing process. This preferred variant is a $15^{th}$ variant of one embodiment, that in one embodiment depends on any of the $12^{th}$ to $14^{th}$ variants of one embodiment.

In another variant of the process, the composite precursor is heated to result in a Vicker's hardness difference of not more than 30%, in one embodiment not more than 25%, between the monolithic metal precursor and the sacrificial outer element, calculated based on the Vicker's hardness of the monolithic metal precursor, between the individual drawing steps. This preferred variant is a $16^{th}$ variant of one embodiment, that in one embodiment depends on the $15^{th}$ variant of one embodiment.

In another variant of the process, step 5) includes an extrusion process. This preferred variant is a $17^{th}$ variant of one embodiment, that in one embodiment depends on the $16^{th}$ variant of one embodiment.

In another variant the extrusion process is carried out with a deformation factor of between 20 and 80%, in one embodiment between 60 and 80%. This preferred variant is a $18^{th}$ variant of one embodiment, that in one embodiment depends on the $17^{th}$ variant of one embodiment.

In another variant of the process, an outer diameter of the sacrificial outer element provided in step 1) and the outer diameter of the formed composite obtained in step 5) have a ratio which is in the range of 60:1 to 2:1; 50:1 to 5:1, or 30:1 to 5:1. This preferred variant is a $19^{th}$ variant of one embodiment, that in one embodiment depends on any of the $1^{st}$ to $18^{th}$ variants of one embodiment.

In another variant of the process, the monolithic metal precursor is formed in step 5) to adopt a smaller dimension without substantially changing its overall geometry. This preferred variant is a $20^{th}$ variant of one embodiment, that in one embodiment depends on any of the $1^{st}$ to $19^{th}$ variants of one embodiment.

In another variant of the process, a further sacrificial core element is provided in step 3). This preferred variant is a $21^{st}$ variant of one embodiment, that in one embodiment depends on any of the $1^{st}$ to $20^{th}$ variants of one embodiment.

In another variant of the process, the shaped metal product is a medical device, such as a medical ring electrode, or a segmented medical electrode, or a part of any one of these. The medical device may be an implantable medical device. The medical device may be configured for electrical stimulation and/or sensing applications of a human or animal subject. This preferred variant is a $22^{nd}$ variant of one embodiment, that in one embodiment depends on any of the $1^{st}$ to $21^{st}$ variants of one embodiment.

A further variant of one embodiment provides a composite for preparing a shaped metal product, including
  i) a sacrificial outer element including a cavity A',
  ii) a monolithic metal element including a cavity B', wherein the monolithic metal element is located in cavity A' of the sacrificial outer element,
  iii) a sacrificial core element, wherein the sacrificial core element is located in cavity B' of the monolithic metal element. This preferred variant is a $23^{rd}$ variant of one embodiment.

In another variant of the composite, the sacrificial outer element and the sacrificial core element are contiguous. This preferred variant is a $24^{th}$ variant of one embodiment, that in one embodiment depends on the $23^{rd}$ variant of one embodiment.

In another variant of the composite, the sacrificial outer element and/or the sacrificial core element include(s) a non-noble metal or non-noble metal alloy, in one embodiment selected from the group of nickel, copper, steel, and alloys of any one of these metals. This preferred variant is a $25^{th}$ variant of one embodiment, that in one embodiment depends on the $23^{rd}$ or $24^{th}$ variant of one embodiment.

In another variant of the composite, the sacrificial outer element and the sacrificial core element include a metal, and wherein the metal of the monolithic metal precursor has a higher standard electrode potential than the metal of the sacrificial outer element and the sacrificial core element. This preferred variant is a $26^{th}$ variant of one embodiment, that in one embodiment depends on any of the $23^{rd}$ to $25^{th}$ variant of one embodiment.

In another variant of the composite, the composite includes a further sacrificial core element that is located in a further cavity of the monolithic metal element. This preferred variant is a $27^{th}$ variant of one embodiment, that in one embodiment depends on any of the $23^{rd}$ to $26^{th}$ variant of one embodiment.

Another variant provides a use of the composite for manufacturing a medical product, in one embodiment an implantable medical device. The medical device may be configured for electrical stimulation and/or sensing applications, such as a medical ring electrode or a segmented medical electrode. This preferred variant is a 28$^{th}$ variant of one embodiment, that in one embodiment depends on any of the 23$^{rd}$ to 27$^{th}$ variant of one embodiment.

Another variant provides a ring electrode obtainable by the process described herein. This preferred variant is a 29$^{th}$ variant of one embodiment, that in one embodiment depends on any of the 1$^{st}$ to 22$^{nd}$ variant of one embodiment.

Furthermore, a process for preparing a ring electrode is provided. The process includes the steps of:
a) providing a monolithic metal precursor,
   wherein the monolithic metal precursor includes an outer tube forming a first cavity of the precursor, and
   wherein the outer tube has a wall including in one section an inner tube forming a second cavity of the precursor;
b) preparing a composite precursor by inserting a first sacrificial core element into the first cavity of the precursor provided in step a) and a second sacrificial core element into the second cavity of the precursor provided in step a);
c) forming the composite precursor obtained in step b) to obtain a formed composite having a smaller outer diameter than the composite precursor obtained in step b);
d) separating a composite disk from the formed composite obtained in step 5);
e) removing the first and the second sacrificial core element from the composite disk obtained in step d).

Also provided is a composite for preparing a ring electrode including
i) a monolithic metal element including an outer tube forming a first cavity,
   wherein the outer tube has a wall including in one section an inner tube forming a second cavity,
ii) a first sacrificial core element, wherein the first sacrificial core element is located in the first cavity of the monolithic metal element, and
iii) a second sacrificial core element, wherein the second sacrificial core element is located in the second cavity of the monolithic metal element.

Another aspect relates to a ring electrode for a medical device,
   wherein the ring electrode is made of a monolithic metal part,
   wherein the ring electrode includes an outer tube forming a first cavity of the electrode,
   wherein the outer tube has a wall including in one section an inner tube forming a second cavity of the electrode, and
   the wall of the outer tube has at least one section having a thickness of below 150 μm.

BRIEF DESCRIPTION OF THE DRAWINGS

The following figures illustrate aspects of the embodiments in connection with some exemplary drawings, wherein.

DETAILED DESCRIPTION

In the following Detailed Description, reference is made to the accompanying drawings, which form a part hereof, and in which is illustrated by way of illustration specific embodiments in which the embodiment may be practiced. In this regard, directional terminology, such as "top," "bottom," "front," "back," "leading," "trailing," etc., is used with reference to the orientation of the Figure(s) being described. Because components of embodiments can be positioned in a number of different orientations, the directional terminology is used for purposes of illustration and is in no way limiting. It is to be understood that other embodiments may be utilized and structural or logical changes may be made without departing from the scope of the present embodiment. The following detailed description, therefore, is not to be taken in a limiting sense, and the scope of the present embodiment is defined by the appended claims.

It is to be understood that the features of the various exemplary embodiments described herein may be combined with each other, unless specifically noted otherwise.

The inventors found that by the process according to one embodiment a shaped metal product can be prepared which is less limited in terms of dimensions, geometry and/or shape. By using the process according to one embodiment, it is possible to uniformly form a scaled-up monolithic metal precursor into a longitudinal direction, in order to prepare a shaped metal product having essentially the same geometry and/or shape as the precursor, but which has a reduced overall diameter. This is achieved by forming a composite including the monolithic metal precursor and sacrificial core elements, which are inserted into the cavities of the precursor. After further processing of the composite including the removal of the sacrificial core elements, the shaped product having the desired dimensions, geometry and/or shape is obtained. The process is very accurate and has very narrow tolerances and/or deviations regarding geometry and/or shape.

The inventors further found that, by the process according to one embodiment, a shaped metal product or a part thereof can be prepared which is less limited in terms of its outer shape. More precisely, by using a circular sacrificial outer element which envelopes a monolithic metal precursor having a non-circular or asymmetric outer shape, it is possible to uniformly form the monolithic metal precursor into a longitudinal direction without significantly changing the overall geometry and/or outer shape of the monolithic precursor (besides its diameter of course). This is achieved by preparing a composite including a sacrificial outer element, which envelopes the monolithic metal precursor, and wherein a sacrificial core element is inserted into a cavity of the monolithic precursor. In a subsequent step, the composite is formed. After further processing of the composite including the removal of the sacrificial outer and core element, the shaped metal product with the desired dimensions, geometry and/or shape is obtained. As already described above, the desired final geometry and shape of the shaped metal product or the part thereof can be fully controlled at the level of a scaled-up monolithic metal precursor.

In case the precursor has an open shape, the sacrificial core elements may be filling and surrounding the precursor, i.e. the sacrificial core element and the outer sacrificial element, may together form a single contiguous object. Thus, in one embodiment, the sacrificial outer element of the sacrificial core element may be provided as a contiguous single object. In this case, the monolithic metal precursor and the contiguous sacrificial element are assembled such that the monolithic metal precursor is surrounded by the material of the contiguous sacrificial element entirely when viewed in a radial cross-section, i.e. surrounding the cross-sectional outer surface of the monolithic metal precursor and filling the cavity B of the monolithic metal precursor.

The general inventive concept of one embodiment is based on the finding that a scaled-up monolithic metal precursor with a desired shape is provided first, and then uniformly formed into a longitudinal direction as part of a composite with sacrificial elements. Thereby, the geometry and/or shape of the monolithic precursor is preserved, and at the same time shaped metal products, e.g. for electrical medical devices, having very small dimensions can be produced.

It is to be understood that the desired final geometry and shape of the shaped metal product can be fully controlled at the level of the scaled-up monolithic metal precursor. The scaled-up monolithic metal precursor can be prepared by a method such as electrically discharge machining (EDM) or metal additive manufacturing (e.g. selective laser melting; selective electron beam melting), which allow for preparing a large variety of different geometries and shapes of a monolithic metal work piece. Hence, the process according to one embodiment gives access to miniaturized shaped metal products with a geometry and/or shape of choice. By conventional techniques, such shaped metal products would only be accessible using very complex and cost intensive processes, if at all possible.

In one aspect, one embodiment refers to a process for preparing a shaped metal product or a part thereof. The process includes the steps of:
1) providing a sacrificial outer element including a cavity A;
2) providing a monolithic metal precursor including a cavity B;
3) providing a sacrificial core element;
4) preparing a composite precursor by inserting the monolithic metal precursor into cavity A of the sacrificial outer element, and by inserting the sacrificial core element into cavity B of the monolithic metal precursor;
5) forming the composite precursor obtained in step 4) to obtain a formed composite having a smaller outer diameter than the diameter of the composite precursor obtained in step 4);
6) separating a composite disk from the formed composite obtained in step 5);
7) removing the sacrificial outer element and the sacrificial core element from the composite disk obtained in step 6).

According to another aspect of one embodiment, a composite for preparing a shaped metal product or a part thereof is provided. The composite includes
i) a sacrificial outer element including a cavity A',
ii) a monolithic metal element including a cavity B', wherein the monolithic metal element is located in cavity A' of the sacrificial outer element,
iii) a sacrificial core element, wherein the sacrificial core element is located in cavity B' of the monolithic metal element.

In a further aspect of one embodiment, a shaped metal product or a part thereof for a medical device is provided, wherein the shaped metal product or the part thereof includes a cavity, and
wherein the shaped metal product or the part thereof is monolithic, and
wherein the shaped metal product or the part thereof, as seen in a radial cross section, has a non-circular outer shape, in one embodiment an open outer shape.

For the purpose of the present embodiments the following terms have the following meanings:

"Monolithic" metal precursor in the meaning of the present embodiments means that the metal precursor is prepared from a single metal piece and/or a seamless metal piece, which in one embodiment has a fully merged or homogeneous structure without boundary lines and/or interfaces between different components. A skilled person can determine whether a metal precursor is a monolithic metal precursor e.g. by scanning electron microscopy (SEM).

A "sacrificial" core element or outer element in the meaning of the present embodiments is a material which can be selectively removed from a composite including the sacrificial material and the material of the monolithic metal precursor (e.g. the formed composite obtained in step 5) or the composite disk obtained in step 7) of the inventive process).

Where an indefinite or definite article is used when referring to a singular noun, e.g., "a", "an" or "the", this includes a plural of that noun unless anything else is specifically stated.

Where the term "comprising" is used in the present description and claims, it does not exclude other elements. For the purposes of the present embodiments, the terms "essentially consisting of" and "consisting of" are considered to be preferred embodiments of the term "comprising". If hereinafter a group is defined to include at least a certain number of embodiments, this is also to be understood to disclose a group, which in one embodiment essentially consists of only of these embodiments, or in one embodiment consists of only of these embodiments.

Terms like "obtainable" or "definable" and "obtained" or "defined" are used interchangeably. This, for example, means that, unless the context clearly dictates otherwise, the term "obtained" does not mean to indicate that, for example, an embodiment must be obtained by, for example, the sequence of steps following the term "obtained" though such a limited understanding is always included by the terms "obtained" or "defined" as a preferred embodiment.

Whenever the terms "including" or "having" are used, these terms are meant to be equivalent to "comprising" as defined hereinabove.

Unless otherwise specified or excluded unambiguously from the context, it is generally possible and is hereby expressly contemplated that features of different embodiments can also be present in each of the other embodiments described herein. It is likewise generally contemplated that all features, which are described herein in connection with a process, can also be used for the products, pre-products (e.g. "composite") and devices described herein, and vice versa. All of these considered combinations are not listed explicitly in all cases only in the interest of a more concise description. Technical solutions, which are obviously equivalent to the features described herein, are also considered to be included in the general scope of the invention.

One aspect of one embodiment refers to a process for preparing a shaped metal product. The process includes the steps of:
variant of the embodiment is a process for preparing a shaped metal product, wherein the process includes the steps of:
1) providing a sacrificial outer element including a cavity A;
2) providing a monolithic metal precursor including a cavity B;
3) providing a sacrificial core element;
4) preparing a composite precursor by inserting the monolithic metal precursor into cavity A of the sacrificial outer element, and by inserting the sacrificial core element into cavity B of the monolithic metal precursor;
5) forming the composite precursor obtained in step 4) to obtain a formed composite having a smaller outer diameter than the diameter of the composite precursor obtained in step 4);
6) separating a composite disk from the formed composite obtained in step 5);
7) removing the sacrificial outer element and the sacrificial core element from the composite disk obtained in step 6).

One embodiment refers to a process for preparing a shaped metal product. According to one preferred embodiment, the process is a process for preparing a shaped metal product.

The inventive process can be used to prepare shaped metal parts for use in medical devices. Such medical devices include active implantable medical devices, such as pulse generators, pacemakers, cardiac resynchronization devices, or other medical electrical sensor or stimulator devices. Active implantable medical devices can be used, for example, in diverse medical applications, such as neuromodulation, cardiac stimulation, deep brain stimulation, spinal cord stimulation or gastric stimulation. One embodiment also provides shaped medical parts and products, such as medical electrodes, for use in these devices and medical applications. The shaped metal part or product may be a ring electrode or segmented electrode, in one embodiment for use in medical applications. The ring electrode may be a circular ring electrode or a hexagonal or octagonal ring electrode. In one embodiment, the ring electrode is a circular ring electrode.

In step 1) of the inventive process, a monolithic metal precursor is provided. The monolithic metal precursor includes a first cavity B of the precursor. The cavity B of the precursor may have a closed structure, i.e. a circular cross-section, or may adopt an open structure. In one example, an open structure may include a U-shaped cross-sectional depression.

The monolithic metal precursor can be prepared by any known method for preparing and/or machining a monolithic metal work piece. In one embodiment, the monolithic metal precursor is prepared by at least one process selected from the group of electrical discharging machining, additive manufacturing, deep-hole drilling, and milling. It is preferred in one embodiment that the monolithic metal precursor is prepared by electrical discharging machining or additive manufacturing (e.g. selective laser melting; selective electron beam melting), and in one embodiment by electrical discharging machining.

In general, the metal of the monolithic metal precursor may be any metal, which is suitable for producing the desired shaped metal product. In one embodiment, the metal of the monolithic metal precursor is a biocompatible metal. The term "biocompatible" in the meaning of the present embodiments is meant to refer to a material which is considered by a person skilled in the art to be safe when being in contact with a living organism (e.g. a human) over a specific period of time (e.g. when used in an implantable medical device). A skilled person knows or can determine whether a metal may be considered biocompatible or not. For example, the biocompatible metal may be a biocompatible metal according to EN ISO 10993.

According to one embodiment, the metal of the monolithic metal precursor includes, in one embodiment consists of, a metal selected from the group consisting of platinum, gold, iridium, steel, titanium, hafnium, niobium, tantalum, cobalt, nickel, chromium, zirconium, rhenium, tungsten, molybdenum, and alloys of any one of these metals. In one embodiment, the metal is selected from the group consisting of nickel cobalt alloy, steel, platinum and platinum iridium alloy. In one embodiment, the steel is a stainless steel. In one embodiment, the nickel cobalt alloy is MP35N. In one embodiment, the platinum iridium alloy is Pt/Ir 10 or Pt/Ir20, and most in one embodiment Pt/Ir 10.

According to one particularly preferred embodiment, the metal of the monolithic metal precursor is a platinum iridium alloy (e.g. Pt/Ir 10 or Pt/Ir 20).

In some embodiments, the monolithic metal precursor includes an alloy selected from the group consisting of MP35N, PtIr10, PtIr20, 316L, 301, and Nitinol.

MP35N is a nickel cobalt alloy including nickel, cobalt, chromium, and molybdenum. A variant of MP35 is described in the industrial standard ASTM F562-13. In one embodiment, MP35 is an alloy that includes 33 to 37% Co, 19 to 21% Cr, 9 to 11% Mo, and 33 to 37% Ni.

PtIr10 is an alloy made of 88 to 92% platinum and 8 to 12% iridium.

PtIr20 is an alloy made of 78 to 82% platinum and 18 to 22% iridium.

316L is an acid-resistant, CrNiMo austenitic steel with approx. 17% Cr; approx. 12% Ni and at least 2.0% Mo. One variant of 316L is described in the industrial standard EN 10088-2. In one embodiment, 316L is an alloy that includes 16.5 to 18.5% Cr, 2 to 2.5% Mo, and 10 to 13% Ni.

301 is a chromium-nickel steel with high corrosion resistance. One variant of 301 is described in the industrial standard DIN 1.4310. In one embodiment, 301 is an alloy that includes 16 to 18% Cr and 6 to 8% Ni.

Nitinol is a nickel-titanium alloy with a shape memory with an ordered-cubic crystal structure and a nickel fraction of approximately 55%, whereby titanium accounts for the remaining fraction. Nitinol has good properties with regard to biocompatibility and corrosion resistance.

Unless specified otherwise, all percentages given herein shall be understood to be mass percentages (weight %).

The monolithic metal precursor may, in principle, have any shape. In some embodiments, the monolithic metal precursor may have a homogeneous shape along one axis, i.e. it has a fixed cross-sectional profile.

The monolithic metal precursor may have a closed structure, e.g. a tubular shape having a circular cross-section, or may adopt an open structure. In one embodiment, the outer shape of the monolithic metal precursor, as seen in a radial cross section, has an open or a closed outer shape. An "open outer shape" means that the monolithic metal precursor contains a cavity B that is not entirely surrounded by the material of the monolithic metal precursor in a radial cross section. For example, a monolithic metal precursor having a C-shaped a radial cross section is considered as having an open outer shape, whereas a monolithic metal precursor having a completely circular, or O-shaped, radial cross section is considered as having a closed outer shape.

A closed outer shape of the monolithic metal precursor may be a cross-sectional shape selected from the list consisting of oval, polygonal, cubic, rectangular, and circular.

For example, the metal precursor may include a tube that includes the cavity B. Such tube may have, for example, an oval, polygonal, cubic, rectangular, or circular radial cross-sectional shape.

In another variant of the process, the monolithic metal precursor has an open outer shape, such as a U-shape, L-shape, T-shape, S-shape or H-shape. This denotes a shape that resembles the mentioned typeface letters.

In another variant of the process, the inner shape of the monolithic metal precursor, as seen in a radial cross section, is a non-circular shape. The "inner shape" of the monolithic metal precursor, as used herein, refers to the non-outward-facing cross-sectional surfaces of the monolithic metal precursor, such as a open recess, dimple, indent, or an open or closed cavity. For example, the inner shape may include a cavity B as described below.

In some embodiments, the sacrificial outer element completely surrounds the outer circumference of the monolithic metal precursor, as seen in a radial cross-sectional view. The sacrificial outer element may have a tube-like shape. The outer shape of the sacrificial outer element may have a circular or oval cross-section, or a differently shaped cross-section. The inner shape of the sacrificial outer element, i.e. the cavity A, may have virtually any shape.

In some embodiments, the sacrificial outer element includes a cavity A having a shape that corresponds to the outer shape of the monolithic metal precursor, so that the monolithic metal precursor can be inserted into cavity A in a form-fit (i.e. positive-locking) manner. In a similar manner, the monolithic metal precursor may include a cavity B having a shape that corresponds to the outer shape of the sacrificial core element.

The geometrical shapes of cavity A and cavity B can be independent from each other. In one embodiment, cavity A and cavity B have a similar geometry, e.g. both cavities have a cylindrical or non-cylindrical shape. In one embodiment, cavity A and cavity B have a different geometry relative to each other. For example, cavity A can be cylindrical and cavity B can be non-cylindrical. In another example, cavity A can have a circular or oval cross-sectional profile, whereas cavity B has a rectangular or triangular radial cross-section.

In some embodiments, cavity A and cavity B can together form a uniform structure as soon as the composite precursor is prepared by inserting the monolithic metal precursor into cavity A of the sacrificial outer element.

In some embodiments, the sacrificial outer element may include a plurality of cavities A. According to these embodiments, a different monolithic metal precursor can be introduced into each one of the plurality of cavities, respectively. Therefore, it is possible to process a plurality of monolithic metal precursors simultaneously in the process according to one embodiment. The plurality of cavities may be overlapping or non-overlapping with respect to each other.

In some embodiments, the monolithic metal precursor may include a plurality of cavities B. Each of these cavities B can be filled with a sacrificial material. For example, if the monolithic metal precursor includes two non-overlapping cavities B, a sacrificial core element can be introduced into each of the two cavities B, respectively.

In step 4) of the inventive process, a composite precursor is prepared by inserting the monolithic metal precursor provided in step 2) into the cavity A of the sacrificial outer element provided in step 1), and inserting the sacrificial core element provided in step 3) into cavity B of the monolithic metal precursor. In particular in those embodiments in which the cavity B has an open outer shape, it is possible, but not necessary, that the sacrificial outer element and the sacrificial core element are provided as a single part. In some embodiments, the sacrificial outer element and the sacrificial core element are provided together as a singular monolithic element.

In principle, the material of the sacrificial outer element and the sacrificial core element may be any material which can be selectively removed from a composite including the sacrificial material and the material of the monolithic metal precursor. Thus, the selection of the material for the sacrificial outer element and the sacrificial core element depends on the metal used for the monolithic metal precursor, and can be selected accordingly. Selective removal of the sacrificial elements can be performed e.g. by melting, chemical etching, or galvanic etching. In some embodiments, the sacrificial outer element and/or the sacrificial core elements are removed by wet chemical etching, e.g. using a strong acid, such as nitric acid or hydrochloric acid or hydrochloric acid According to one embodiment, the sacrificial outer element and/or the sacrificial core element include(s), in one embodiment consists of, a non-noble metal or non-noble metal alloy. A "non-noble" metal or metal alloy in the meaning of the present embodiments is a metal which is not selected from the group of ruthenium, rhodium, palladium, silver, osmium, iridium, platinum, gold, mercury, and alloys of the foregoing metals. According to one embodiment, the sacrificial outer element and the sacrificial core element include a non-noble metal or non-noble metal alloy.

In one embodiment, the non-noble metal or non-noble metal alloy is selected from the group of Wood's metal, zinc, tin, nickel, copper, steel, and alloys of any one of these metals. "Wood's metal" is a metal alloy including bismuth, lead, tin and cadmium, and which has a melting point below 100° C. The non-noble metal or non-noble metal alloy may react with acids, in one embodiment strong acids (e.g. sulfuric acid, Hydrochloric Acid, nitric acid).

The sacrificial outer element and the sacrificial core element are also referred to as "sacrificial elements" herein, which intends to include both each of the elements individually, or both of them collectively. According to one preferred embodiment, the sacrificial outer element and/or the sacrificial core element include(s), in one embodiment consist(s) of, a metal selected from the group of nickel, copper, steel, and alloys of any one of these metals. According to one preferred embodiment, the sacrificial outer element and the sacrificial core element include, in one embodiment consist of, a metal selected from the group of nickel, copper, steel, and alloys of any one of these metals. In one embodiment, the sacrificial outer element and/or the sacrificial core element include(s), in one embodiment consists of, a metal selected from the group of nickel, steel (e.g. stainless steel AISI 316 L), and alloys of these metals.

The inventors surprisingly found that a metal selected from the group of nickel, steel, and alloys of these metals is particularly well-suited as the sacrificial outer element and/ or the sacrificial core element, because the materials illustrate a comparatively low diffusion into the monolithic metal precursor during the forming step, and particularly during intermediate annealing steps between or during a drawing process.

The material, in one embodiment the metal, of the outer sacrificial element and the sacrificial core element may be the same or different. In one embodiment, the materials of the core elements are different. According to one preferred embodiment, the outer sacrificial element includes, in one embodiment consists of, nickel and the sacrificial core element includes, in one embodiment consists of, steel.

According to one preferred embodiment, the monolithic metal precursor includes, in one embodiment consists of, platinum or a platinum iridium alloy, the sacrificial outer element includes, in one embodiment consists of, nickel and the sacrificial core element includes, in one embodiment consists of, steel. In another preferred embodiment, the monolithic metal precursor includes, in one embodiment consists of, platinum or a platinum iridium alloy, and the sacrificial elements includes, in one embodiment consists of, nickel. The sacrificial elements may be provided as a single monolithic element in the latter embodiment.

The selective removability of the sacrificial elements from the composite including the monolithic metal precursor, in one embodiment the formed composite obtained in step 4) or the composite disk obtained in step 6), may be based on a difference in melting point of the materials and/or a difference in chemical reactivity of the materials (e.g. reactivity towards acids or bases). For example, the material of the sacrificial elements may have a lower melting point than the monolithic metal precursor, so that the sacrificial elements may be removed by a melting step. Additionally or alternatively, the material of the sacrificial outer element and/or the sacrificial core element may have a higher chemical reactivity, in one embodiment towards acids, than the monolithic metal precursor, so that the sacrificial elements may be removed by an acid treatment step. A removal of the sacrificial elements based on a difference in chemical reactivity is preferred over a removal based on a difference in melting points.

According to one preferred embodiment, the sacrificial elements include, in one embodiment consist of, a metal, and the metal of the monolithic metal precursor has a higher, i.e. more positive, standard electrode potential than the metal(s) of the sacrificial core elements. A skilled person knows what the standard electrode potential of a mental is or can look it up. According to the Compendium of Chemical Terminology by the IUPAC, the standard electrode potential is the value of the standard electromotive force of a cell in which molecular hydrogen understand the pressures oxidized to selected protons at the left-hand electrode.

According to one embodiment, the sacrificial core element inserted in step 4) has the dimensions of the cavity B of the monolithic metal precursor provided in step 2), and/or the monolithic metal precursor inserted in step 4) has the dimensions of the cavity A of the sacrificial outer element provided in step 1). "Having the dimensions of" the cavity can be understood in that the monolithic metal precursor and/or the sacrificial core element have near net shape of the cavity A or second cavity B, respectively. According to one embodiment, the sacrificial core element inserted in step 4) has the dimensions of the cavity B of the monolithic metal precursor provided in step 2), and/or the monolithic metal precursor inserted in step 4) has essentially the dimensions of the cavity A of the sacrificial outer element provided in step 1). In one embodiment, the diameter of the sacrificial core element inserted in step 4) is smaller than the diameter of the cavity B of the monolithic metal precursor by a factor in the range of 0.01 to 5%, in one embodiment in the range of 0.01 to 3%. In one embodiment, the diameter of the monolithic metal precursor inserted in step 4) is smaller than the diameter of the cavity A of the sacrificial outer element by a factor in the range of 0.01 to 5%, in one embodiment in the range of 0.01 to 3%.

The diameter refers to the respective outer diameter of a structure. In case the respective element has a non-circular cross section, the "diameter" is assumed to be the maximum width of the element in a radial cross-section, as further explained herein below with reference to FIG. 8.

The first sacrificial elements may be prepared by any suitable method, such as drawing processes, rolling processes, extrusion, milling, and the like.

The individual elements may be inserted into the cavities A and B by any suitable methods known in the art.

In step 5) of the inventive process, the composite precursor obtained in step 4) is formed to obtain a formed composite having a smaller outer diameter than the composite precursor obtained in step 4).

The forming in step 5) may include at least one process selected from the group of drawing processes, swaging processes, hammering processes and rolling processes. In one embodiment, the forming process is carried out stepwise. The forming parameters in step 5) are selected in such a way that in all individual forming steps the stress is introduced into the core of the composite so that all parts of the composite are uniformly deformed into the longitudinal direction during step 5).

According to one embodiment, the forming in step 5) includes an extrusion process.

Extrusion is a manufacturing process in which a cylindrical billet inside a closed cavity is forced to flow through a die of a desired cross-section. These fixed cross-sectional profile extruded parts are called "extrudates" and pushed out using either a mechanical or hydraulic press.

According to one embodiment, the forming in step 5) includes a drawing process. In one embodiment, the drawing process is carried out stepwise, i.e. with multiple individual drawing steps. In one embodiment, the drawing process is carried out with a deformation factor of between 5 and 40%, in one embodiment between 15 and 30%, per individual drawing. It is further preferred that the drawing process is carried out with a die cast having a total included angle $2\alpha$ in the range of from 5 to 20°, in one embodiment from 5 to 15°. According to one preferred embodiment, the forming in step 5) includes a drawing process, which is carried out with a deformation factor of between 5 and 40%, in one embodiment between 15 and 30%, per individual drawing, and with a die cast having a total included angle $2\alpha$ in the range of from 5 to 20°, in one embodiment from 5 to 15°. It is preferred in one embodiment that the deformation factor is in the range of above 20 to 25%, per individual drawing, with a die cast having a total included angle $2\alpha$ in the range of from 12 to 15° (e.g. 12°).

According to one embodiment, the forming in step 5) includes at least one step of annealing and/or recrystallizing an intermediate formed composite. According to one preferred embodiment, the forming in step 5) includes a drawing process, wherein the drawing process includes at least one step of annealing and/or recrystallizing an intermediate formed composite.

Annealing and/or recrystallization steps in metal forming processes are known to the skilled person and can be adjusted based on selected materials of the monolithic metal precursor provided in step 2) and the sacrificial elements. The steps of annealing and/or recrystallizing are carried out in view of the critical degree of transformation of the materials and/or the recrystallization temperature of the materials used in the process. For example, if nickel is used as the sacrificial elements, the critical degree of transformation is about 60% and the recrystallization temperature is about 700° C.

In some embodiments, it is preferred that the hardness of the monolithic metal precursor and the sacrificial elements has a similar value during the step of forming the composite precursor, in particular during the annealing and/or recrystallization steps of a drawing process. This can be achieved by choosing an appropriate temperature while forming the composite precursor, e.g. during these annealing and/or recrystallization steps.

The Vicker's hardness of different materials may have a different temperature dependence. Thus, the hardness difference between two or more different materials may be minimized by simultaneously heating them to the same temperature. The Vicker's hardness of different materials at different temperatures can be measured as described herein, or can be derived from the relevant literature. The optimum temperature depends on the specific materials that are used for the monolithic metal precursor and the sacrificial elements.

Minimizing the hardness difference between the monolithic metal precursor at the sacrificial elements may result in a more homogeneous deformation of the composite precursor.

In some embodiments of the process, the composite precursor is heated to result in a Vicker's hardness difference of not more than 30%, in one embodiment not more than 25%, between the monolithic metal precursor and the sacrificial outer element, calculated based on the Vicker's hardness of the monolithic metal precursor, between the individual drawing steps.

In some embodiments of the process, the composite precursor is heated to result in a Vicker's hardness difference of not more than 30%, in one embodiment not more than 25%, between the monolithic metal precursor and the sacrificial core element, calculated based on the Vicker's hardness of the monolithic metal precursor, between the individual drawing steps.

In some embodiments of the process, the composite precursor is heated to result in a Vicker's hardness difference of not more than 30%, in one embodiment not more than 25%, between the monolithic metal precursor and the sacrificial outer element, and between the monolithic metal precursor and the sacrificial core element, calculated based on the Vicker's hardness of the monolithic metal precursor, respectively, between the individual drawing steps.

Hardness is a measure of the resistance to localized plastic deformation induced by either mechanical indentation or abrasion. Vicker's hardness can be measured my microindentation. In this method, a diamond probe is pressed into the material to be tested while recording a force-distance measurement by HRC measuring the diagonals of the remaining mark/imprint. From the resulting data, the mechanical hardness can be determined. A suitable device for measuring Vicker's hardness is the Anton Paar MHT-10 Microhardness Tester. The indentation depth should not exceed 10% of the thickness of the tested material. Vicker's hardness can be determined according to the standard DIN EN ISO 6507-4:2018.

In forming step 5), the outer diameter of the monolithic metal precursor provided in step 2) being part of the composite obtained in step 4) is decreased.

According to one preferred embodiment, the outer diameter of the composite precursor obtained in step 4) and the outer diameter of the formed composite obtained in step 5) have a ratio which is in the range of 60:1 to 2:1, in one embodiment in the range of 30:1 to 5:1. According to one preferred embodiment, the formed composite obtained in step 5) has an outer diameter in the range of 0.2 to 5 mm, in one embodiment of 0.5 to 2 mm.

In some embodiments, the monolithic metal precursor is formed in step 5) to adopt a smaller dimension without substantially changing its overall geometry. This means that the relative cross-sectional dimensions, such as the respective ratios of the diameters a1, b1 and d1, referring to the outer cross-sectional diameters of the monolithic metal precursor, the cavity B and the sacrificial outer element, respectively, remain essentially constant, as illustrated below with reference to FIG. 5 in more detail. This advantage may be achieved by virtue of using the sacrificial elements in connection with a suitable deformation process, such as a drawing or extrusion process.

In step 6) of the inventive process, a composite disk is separated from the formed composite obtained in step 5).

The composite disk may be separated by any method which is suitable for cutting the material of the monolithic metal precursor and of the sacrificial core elements. For example, a composite disk may be separated from the formed composite obtained in step 5) by wire erosion or laser cutting.

In step 7) of the inventive process, the sacrificial outer element and the sacrificial core element are removed from the composite disk obtained in step 6).

Step 7) of the inventive process depends on the material which is used for the sacrificial outer element and the sacrificial core element. According to one embodiment, the sacrificial outer element and the sacrificial core element is removed in step 7) by melting out, etching, corrosion, or combinations thereof. In one embodiment, the sacrificial outer element and the sacrificial core element is removed in step 7) by melting out, etching, corrosion, or combinations thereof. More in one embodiment, the first sacrificial elements are removed in step 7) by etching, corrosion, or combinations thereof. Such processes are known to the skilled person, and a skilled person can select the method of removing in step 7) in view of the materials used for the sacrificial elements.

For example, in case the sacrificial outer element and the sacrificial core element includes, in one embodiment consists of, a metal having a melting point below 500° C. (e.g. Wood's metal or a zinc or tin alloy), the sacrificial outer element and the sacrificial core element may be melted out by subjecting the composite disk obtained in step 6) to a temperature above the melting point of one of these materials, in one embodiment in the range of 50 to 500° C. The melting out of the sacrificial elements is in one embodiment carried out with vacuum support to overcome the capillary force.

A preferred option is to remove the sacrificial outer element and the sacrificial core element by treating the composite disk obtained in step 6) by an acid (e.g. sulfuric acid, hydrochloric acid, nitric acid) or a base. For example, copper as the sacrificial outer element and the sacrificial core element may be removed by treatment with nitric acid.

There are also selective etching solutions available for a specific metal being useful as the sacrificial outer element and the sacrificial core element. Such etching solutions are known to the skilled person and can be selected accordingly.

In case the materials of sacrificial outer element and the sacrificial core element are different from each other, it is possible to first selectively remove the sacrificial outer element and then selectively remove the sacrificial core element, or vice versa.

In case, the monolithic metal precursor includes further sacrificial elements, step 7) further includes removing the at least one further sacrificial element from the composite disk obtained in step 6).

Step 7) can be performed before or after step 6). In some embodiments, it is preferred that step 7) is performed after step 6).

In addition to the essential steps 1) to 7), the inventive process may further include additional process steps of post-processing the shaped metal part obtained in step 7). For example, after step 7), the process may include a further step of washing (e.g. HCl washing) and drying the shaped metal part. It is also possible to subject the shaped metal part obtained in step 7) to a surface finishing step such as polishing, sanding, and/or grinding. In one embodiment, the inventive process includes after step 7) the washing, in one embodiment washing with HCl, and drying of the shaped metal part followed by a surface finishing step, in one embodiment polishing.

The shaped metal part prepared by the inventive process is in one embodiment suitable for use in a medical device, and more in one embodiment an active implantable medical device (AIMD)) Preferred AIMDs are, for example, cardiac pacemakers, cardiac defibrillators, neurostimulators, cochlear implants, implantable cardioverters, nerve, brain, organ or muscle stimulators as well as implantable monitoring devices, hearing aids, retinal implants, muscle stimulators, implantable drug pumps, artificial hearts, bone growth stimulators, prostate implants, stomach implants or the like. In one embodiment, the active implantable medical device is a cardiac pacemaker or a neuromodulator.

In some embodiments, the shaped metal part prepared by the inventive process may also be suitable for use in a lead for a medical device, in one embodiment an active implantable medical device.

Another object of one embodiment refers to a composite for preparing a shaped metal product, including
  i) a sacrificial outer element including a cavity A',
  ii) a monolithic metal element including a cavity B', wherein the monolithic metal element is located in cavity A' of the sacrificial outer element,
  iii) a sacrificial core element, wherein the sacrificial core element is located in cavity B' of the monolithic metal element.

In some embodiments, the sacrificial outer element and the sacrificial core element are contiguous as described above in the context of the process of the present embodiments, i.e. they are provided is a single sacrificial element which is surrounding the cross-sectional profile of the monolithic metal precursor, and filling the cavity B' in the monolithic metal element.

Regarding the material, geometry, and shape of the monolithic metal element as well as the sacrificial elements (i.e. the sacrificial outer element and the sacrificial core element), it is referred to the specification of the inventive process above. The embodiments, and preferred embodiments, of the monolithic metal precursor provided in the inventive process are also embodiments, and preferred embodiments, of the monolithic metal element of the composite according to one embodiment. The embodiments, and preferred embodiments, of the sacrificial elements according to the inventive process are also embodiments, and preferred embodiments, of the sacrificial elements of the composite according to one embodiment. In this context, it is reiterated that the inventive process has the advantage that the geometry and shape of the monolithic metal precursor provided in step 2) is essentially maintained during the later steps of the process. For example, the formed composite obtained in step 5) of the inventive process essentially includes a scaled-down version of the monolithic metal precursor of step 2).

The composite includes a monolithic metal element including a cavity B', wherein the sacrificial outer element includes a cavity A'. The outer shape of the monolithic metal element may essentially correspond to the inner shape of the sacrificial outer element, i.e. the cavity A'.

In one embodiment, an outer wall of the composite has at least one section having a thickness of below 150 µm, and in one embodiment in the range of 10 to 100 µm. It is further preferred that the composite has an outer diameter in the range of 0.2 to 5 mm, and in one embodiment of 0.5 to 2 mm, and/or the cavity A' formed by the sacrificial outer element has an inner diameter in the range of 0.05 to 4.8 mm, and in one embodiment 0.1 to 1.8 mm, and/or the cavity B' formed by monolithic metal element has an inner diameter in the range of 0.01 to 1.0 mm, and in one embodiment 0.05 to 0.3 mm.

The composite and/or the shaped metal product may include a monolithic metal. "Monolithic metal" means that the metal of the composite and/or the shaped metal product is a single metal piece and/or a seamless metal piece, which in one embodiment has a fully merged or homogeneous structure without boundary lines and/or interfaces between different components. However, it is to be understood that this does not exclude that the composite and/or the shaped metal product includes a coating. A "coating" for a ring electrode in the meaning of one embodiment is a thin layer, in one embodiment in the range of 0.1 to below 10 µm. Thus, the monolithic metal ring electrode may include a metal coating, a metal oxide coating or a metal nitride coating. The metal of the metal coating metal oxide coating or a metal nitride coating may be the same or different to the metal of the ring electrode. The monolithic metal of the ring electrode may also be coated with a polymer coating. The monolithic metal of the ring electrode may also be surface structured, e.g. laser structured. In principle, the ring electrode of one embodiment may include all surface modifications, which are commonly applied to ring electrodes being used in medical devices, and particularly active implantable medical devices.

It is to be understood that the monolithic metal precursor is not limited in that it may only include one cavity as described above. In other words, it is possible, and in certain embodiments preferred, that the monolithic metal precursor includes at least one further inner cavity. The design, shape, and dimensions of the at least one cavity may be the same or different than the first cavity of the monolithic metal precursor. According to one embodiment, the monolithic metal precursor includes two or more cavities, such as three, four or more than four cavities.

Another aspect of one embodiment refers to a medical device including a shaped metal product according to one embodiment. The medical device may be a lead for an active implantable medical device (AIMD). The medical device may also be an active implantable medical device) Preferred AIMDs are, for example, cardiac pacemakers, cardiac defibrillators, neurostimulators, cochlea implants, implantable cardioverters, nerve, brain, organ or muscle stimulators as well as implantable monitoring devices, hearing aids, retinal implants, muscle stimulators, implantable drug pumps, artificial hearts, bone growth stimulators, prostate implants, stomach implants or the like. In one embodiment, the active implantable medical device is a cardiac pacemaker or a neuromodulator. A particularly preferred AIMD includes a segmented stimulation electrode or segmented sensing electrode.

Embodiments are further illustrated by the examples illustrated in the appended drawings. It is to be understood that the drawings illustrate only specific examples, and shall not be construed as limiting the scope of the present invention.

Figure 1:
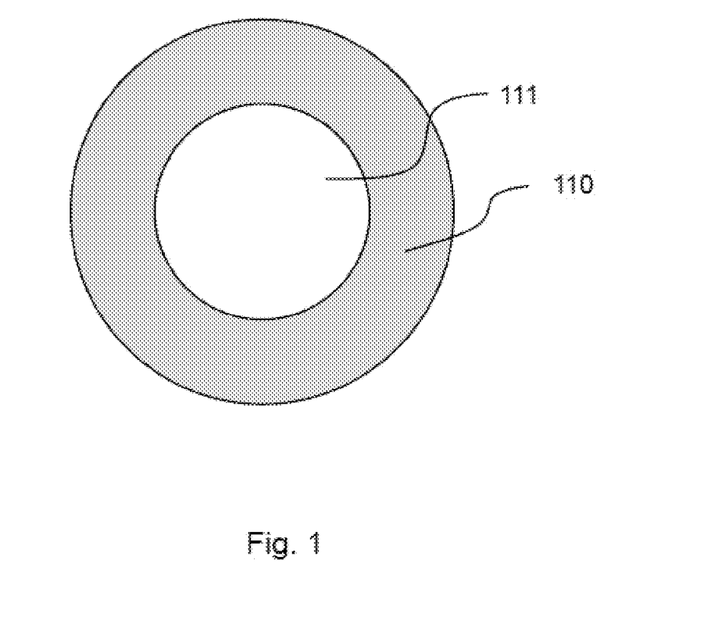
FIG. 1 illustrates an image of a sacrificial outer element in a top view/cross section view.

FIG. 1 illustrates an image of a sacrificial outer element in a top view/radial cross section view. In this example, the sacrificial outer element 110 has a tube-like shape with a circular cross-section and is made of nickel. The sacrificial outer element 110 includes a cavity A 111, which has a circular cross-section in this particular example.

Figure 2:
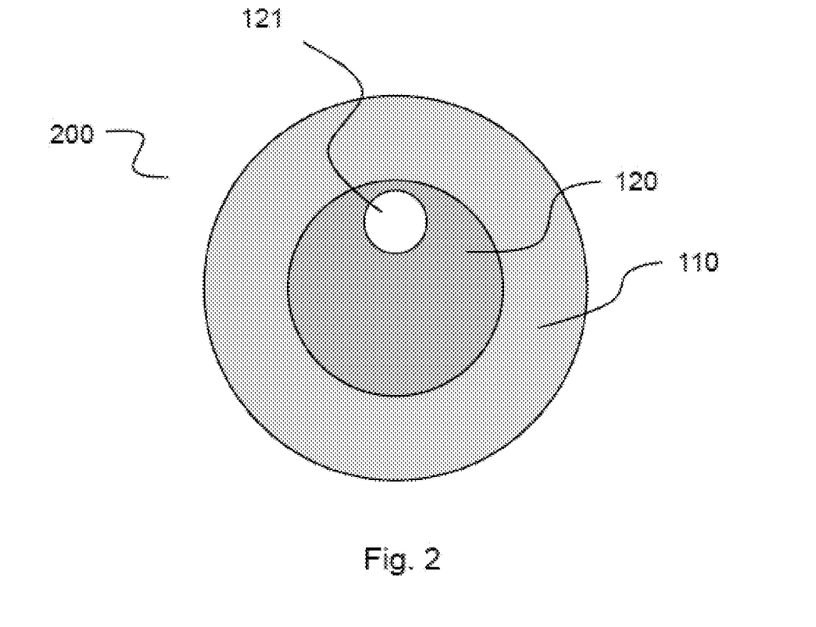
FIG. 2 illustrates a cross-sectional image of a monolithic metal precursor that is inserted into a cavity of a sacrificial outer element.

FIG. 2 illustrates a cross-sectional image of a monolithic metal precursor 120 made of PtIr10 alloy that is inserted into a cavity A 111 of a sacrificial outer element 110. The monolithic metal precursor 120 has been arranged inside the cavity A of the sacrificial outer element 110 in a form-fit (positive-locking) manner, thus forming a composite precursor 200 from these two components. There is virtually no remaining open space or gap between the sacrificial outer element 110 and the monolithic metal precursor 120. The monolithic metal precursor 120 includes a cavity B 121, which in this example has a cylindrical shape with a circular cross-section.

Figure 3:
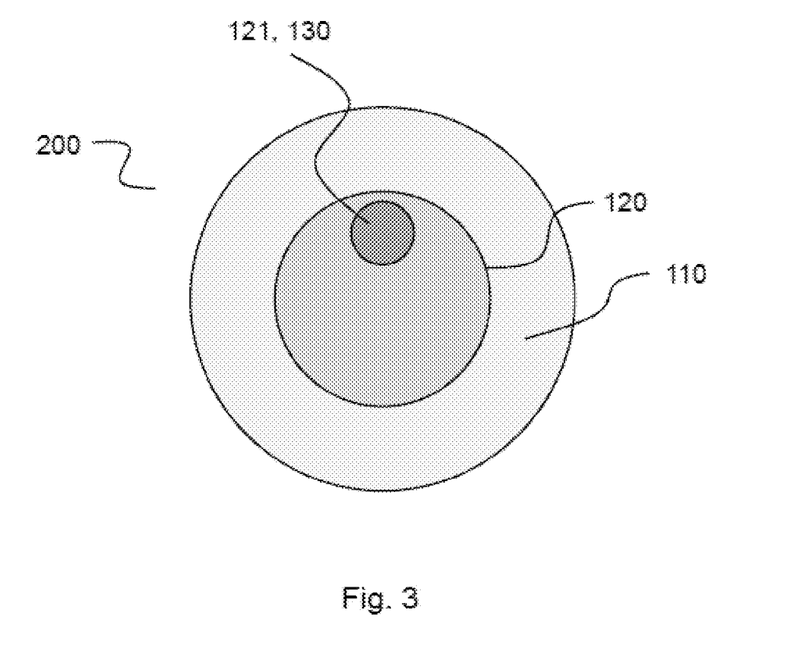
FIG. 3 illustrates a cross-sectional image of a composite precursor.

FIG. 3 illustrates a cross-sectional image of a composite precursor 200, which further includes a sacrificial core element 130. The sacrificial core element 130 has been inserted into the cavity B 121 in a form-fit manner, so that virtually no open-space remains between the sacrificial core element 130 and the monolithic metal precursor 120, i.e. the sacrificial core element 130 fills out the cavity B 121 essentially completely. A composite precursor 200 like illustrated in this figure may subsequently be subjected to a forming process, such as a drawing process, to reduce the cross-sectional dimensions of the monolithic metal precursor in a homogeneous manner. During this process, the sacrificial core element and the sacrificial outer element act as supporting structures which facilitate a homogeneous deformation of the monolithic metal precursor, wherein the overall geometry of the monolithic metal precursor does not substantially change, except for a homogeneous reduction of its radial, cross-sectional dimensions, as further illustrated in FIG. 5 below.

Figure 4:
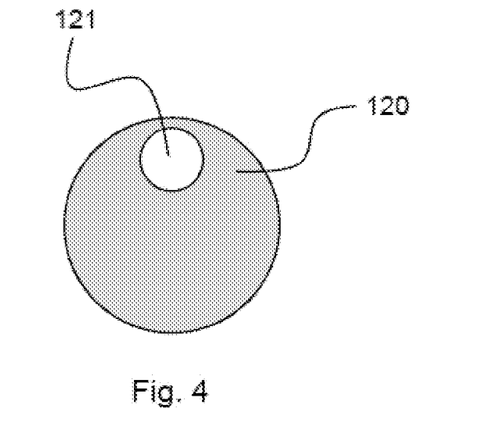
FIG. 4 illustrates an image of a radial cross section of a shaped metal object prepared by the inventive process.

FIG. 4 illustrates an image of a radial cross section of a shaped metal object prepared by the inventive process from a composite precursor like the one illustrated in FIG. 3. The shaped metal object includes a scaled-down equivalent of the original monolithic metal precursor 120. The sacrificial outer element and the sacrificial core element have been removed by chemical etching, thus producing a shrunken, scaled-down equivalent of the original monolithic metal precursor, but without any surrounding sacrificial material, and an empty cavity B 121. The cavity B 121 is also smaller in its radial dimension compared to the original monolithic metal precursor.

Figure 5:
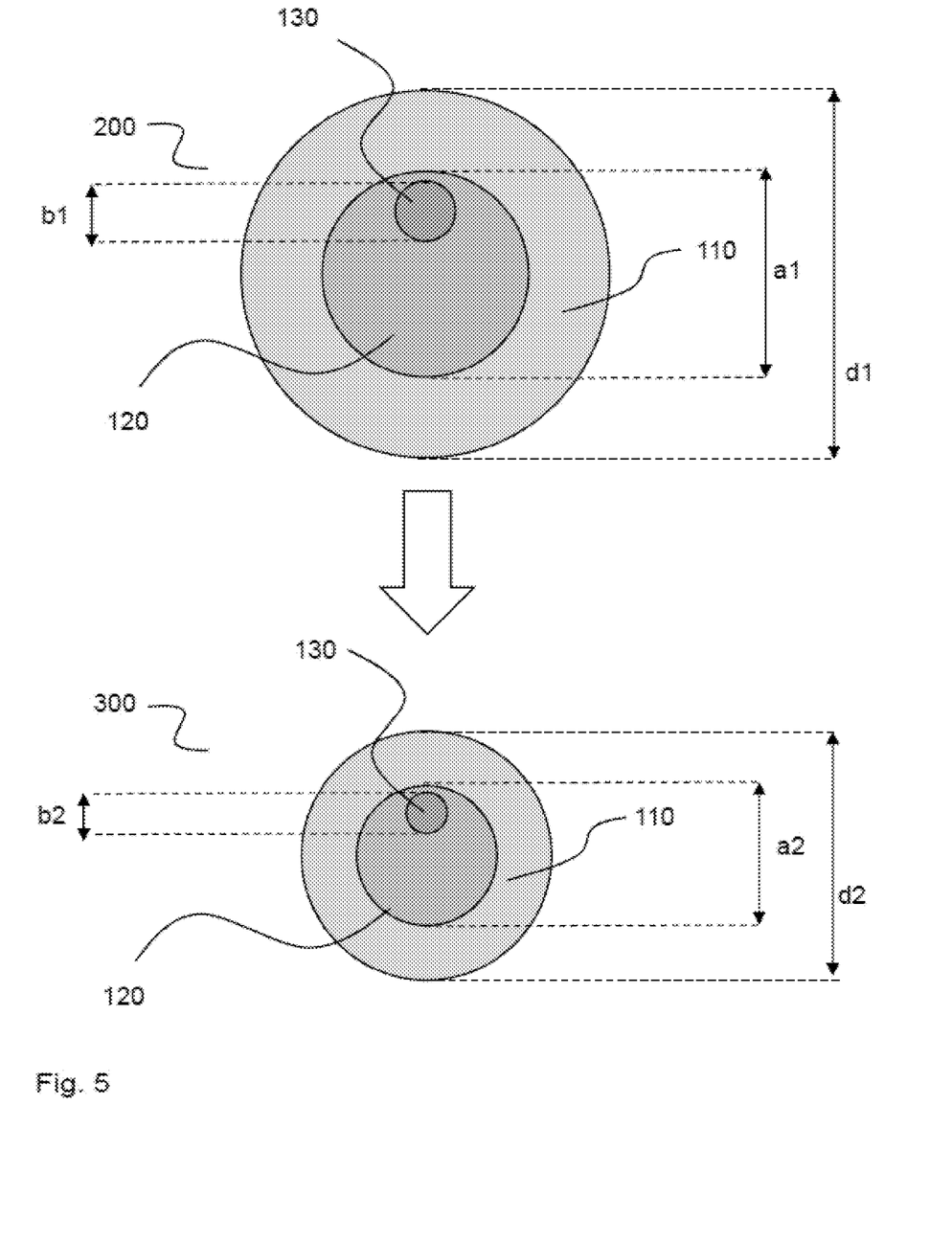
FIG. 5 illustrates a process step of forming a composite precursor prepared in step 4 to obtain a formed composite having a smaller outer diameter.

FIG. 5 illustrates a process step of forming a composite precursor 200 to obtain a formed composite 300 having a smaller outer diameter. The upper image illustrates the composite precursor 200 before the deformation step 5). The composite precursor includes a monolithic metal precursor 120 having an outer diameter a1, surrounded by an outer sacrificial element 110 having an outer diameter d1. The monolithic metal precursor 120 includes a cavity that is filled with a sacrificial core element 130, which has an outer diameter b1.

The lower image of FIG. 5 illustrates a formed composite 300 that has been obtained by subjecting the composite precursor 200 according to the upper image to a drawing process. The monolithic metal precursor 120 now has a smaller outer diameter a2, the outer sacrificial element 110 has a smaller outer diameter d2, and the sacrificial core element 130 has a smaller outer diameter b2. In this example, all of these outer diameters have been reduced essentially by the same factor in comparison to their original diameters, respectively. Accordingly, in this embodiment, there is an equal, common shrink factor defined as a1:a2=b1:b2=d1:d2.

Figure 6:
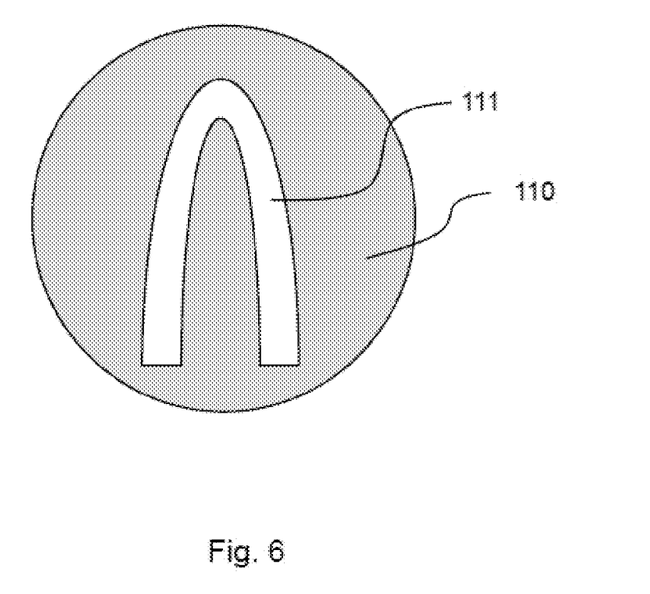
FIG. 6 illustrates a cross-sectional image of a sacrificial outer element.

FIG. 6 illustrates a cross-sectional image of another embodiment of a sacrificial outer element. In this case, the sacrificial outer element 110 has an outer shape with a regular, circular cross-section, but its inner shape, which defines the cavity A 111, has a more irregular, non-circular geometry.

Figure 7:
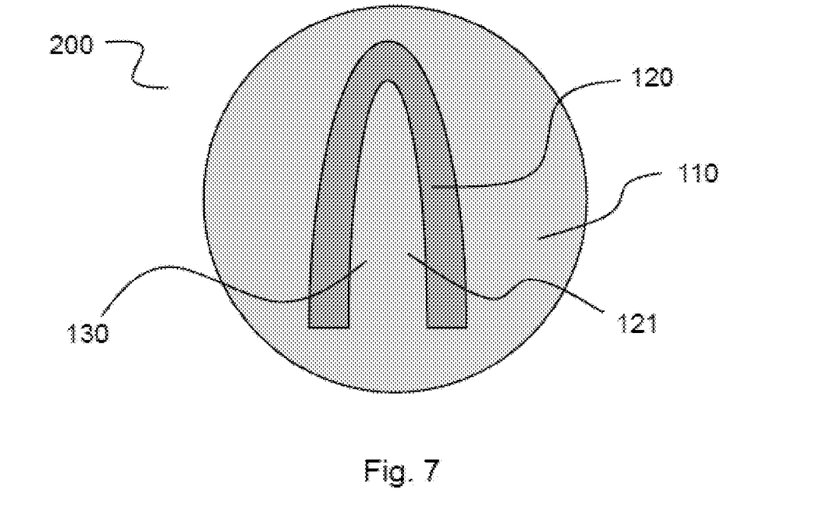
FIG. 7 illustrates a cross-section of a monolithic metal precursor inserted into the sacrificial outer element according to FIG. 6.

FIG. 7 illustrates a cross-section of a monolithic metal precursor 120 inserted into the sacrificial outer element 110 according to FIG. 6. The monolithic metal precursor 120 has a shape which is corresponding to the cavity A 111 of the sacrificial outer element 110 according to FIG. 6. Thus, the monolithic metal precursor can be integrated seamlessly into the cavity A of the sacrificial outer element in a form-fit manner.

Figure 8:
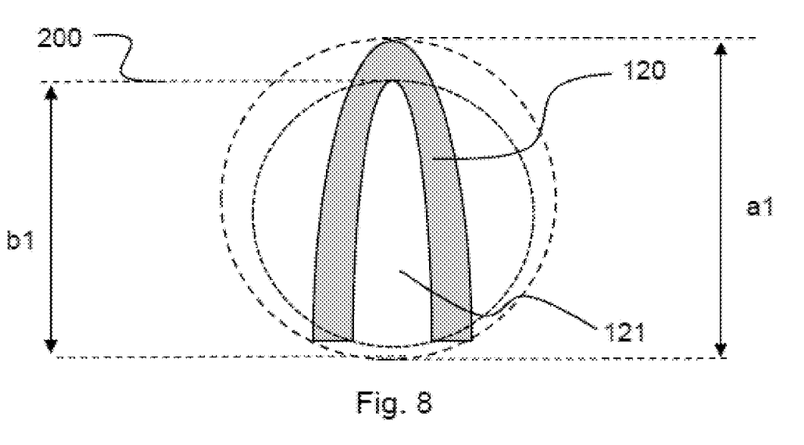
FIG. 8 depicts a monolithic metal precursor having an open outer shape.

FIG. 8 depicts a monolithic metal precursor having an open outer shape. The dimensions of the monolithic metal precursor 120 and the cavity B 121 are provided in analogy to FIG. 5 as described above. Thus, the term "diameter" is used herein also for elements having a non-circular cross-section. It can be determined by drawing a circle around the element in a way that the circle has the smallest possible diameter while still including the entire cross-section of the geometry of the respective element, e.g. the monolithic metal precursor 120 or the cavity B 121. This essentially corresponds to the maximum width of the respective element in a radial cross-section. Therefore, such "diameter" of an element can also be determined by measuring its maximum radial width using a suitable instrument, such as a caliper.

Accordingly, as used herein, the monolithic metal precursor 120 has a "diameter" a1, and the cavity B 121 has a "diameter" b1.

In the process of one embodiment, each of these "diameters" a1, b1 and d1 of a composite precursor can be homogeneously reduced by the same, or substantially the same, shrink factor, in analogy to the description of FIG. 5 above.

Figure 9:
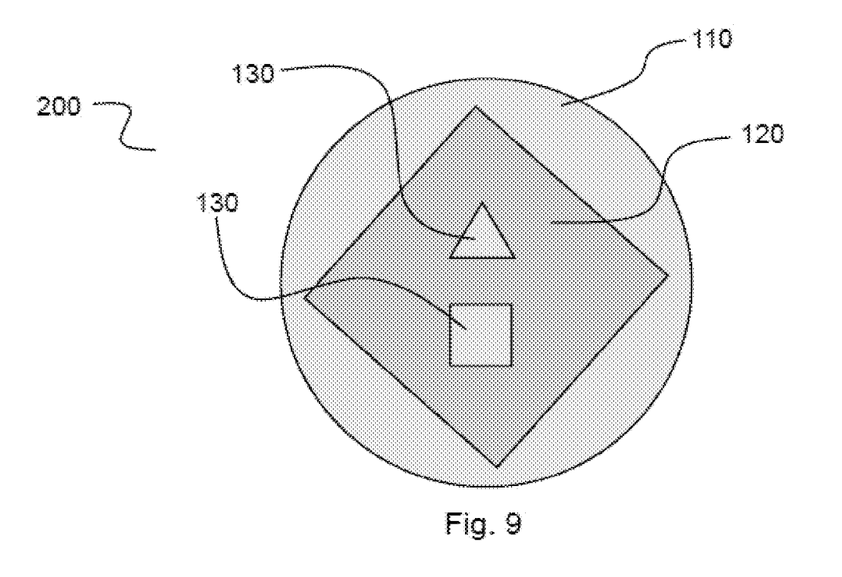
FIG. 9 illustrates an example of a composite precursor having two differently shaped sacrificial core elements.

FIG. 9 illustrates a schematic of a cross-section of another embodiment of a composite precursor 200. In this embodiment, the monolithic metal precursor 120 has a square-shaped cross-section, and includes two sacrificial core elements 130 having different shapes, in this case a triangular cross-section and a square cross-section. The sacrificial core elements are embedded inside two cavities B which are shaped to match the outer shapes of the respective sacrificial core elements, respectively. The monolithic metal precursor 120 is embedded inside a sacrificial outer element 110, which has a circular outer shape, and includes a cavity A with a square-shaped cross-section corresponding to the outer shape of the monolithic metal precursor. The manufacturing of such a composite precursor is described in further detail in the following example.

Example 1

An example design was produced using the following steps and conditions. The composite was built from an outer sacrificial part, made from nickel. A rectangular inner main part with a rectangular cavity and a triangular cavity, made from PtIr10%, two inner sacrificial cores, one rectangular, one triangular, made from nickel was prepared according to the geometries drawn to scale in FIGS. 10 and 11, all by electrical discharge machining (EDM), respectively. The outer sacrificial nickel part as well the inner nickel sacrificial parts were annealed at 500° C. for 30 min, resulting in a hardness of 250 HV. The PtIr main part has been used hard drawn, having a hardness of 220 HV. All the parts had a surrounding gap of 0.05 mm to each other. The parts were then drawn in a first step, D 14.5 mm to 14.2 mm, using a die with a die angle of 2 alpha=10°. Then the composite was annealed at 500° C. for 30 min, resulting in a nickel hardness of 250 HV and a PtIr hardness of 200 HV. Then the composite was drawn, with each drawing step performed with a 15% cross area reduction and a die angle of 10°. After each fourth drawing step, the composite was annealed at 500° C. for 30 min. The composite was drawn down to a diameter of 1.74 mm.

The same procedure was performed again using a rectangular inner main part made of PtIr11%.

The starting dimensions of the composite precursor are compared with the end dimensions of the formed composite in Table 1. An essentially uniform shrink factor of about 8.3:1 was achieved for all dimensions. Except for the desired homogeneous shrinking of the dimensions, the geometry of the original shape of the composite precursor was substantially maintained in the formed composite. A shaped metal product was obtained by cutting the formed composite and removing the sacrificial materials etching as described in US2019255317A1, which is hereby incorporated by reference in its entirety.

Figure 10:
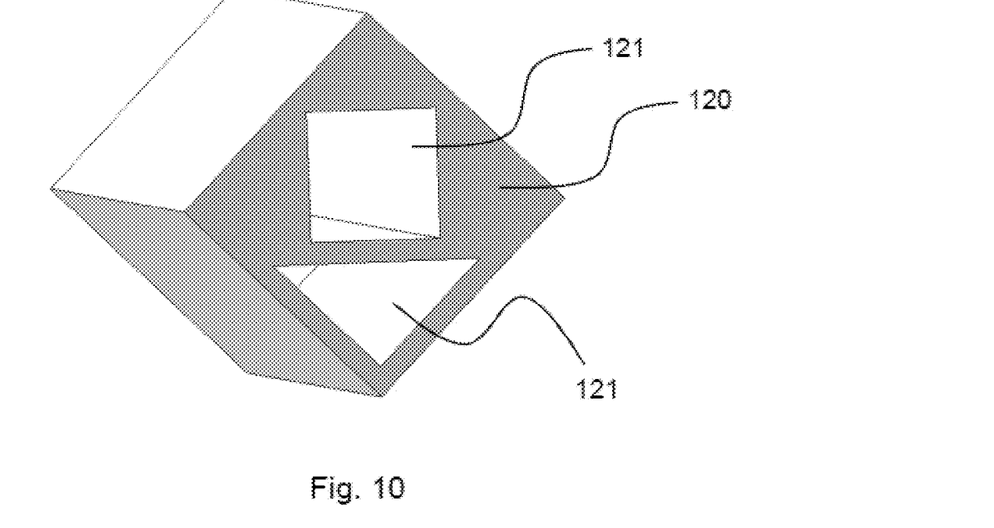
FIG. 10 illustrates a monolithic metal precursor according to Example 1.

FIG. 10 illustrates a drawn-to-scale isometric view of the monolithic metal precursor 120 according to this example, including two differently shaped cavities B 121, having a square-shaped and triangular-shaped radial cross-section, respectively. This precursor has been made from PtIr10% or PtIr11%, respectively.

Figure 11:
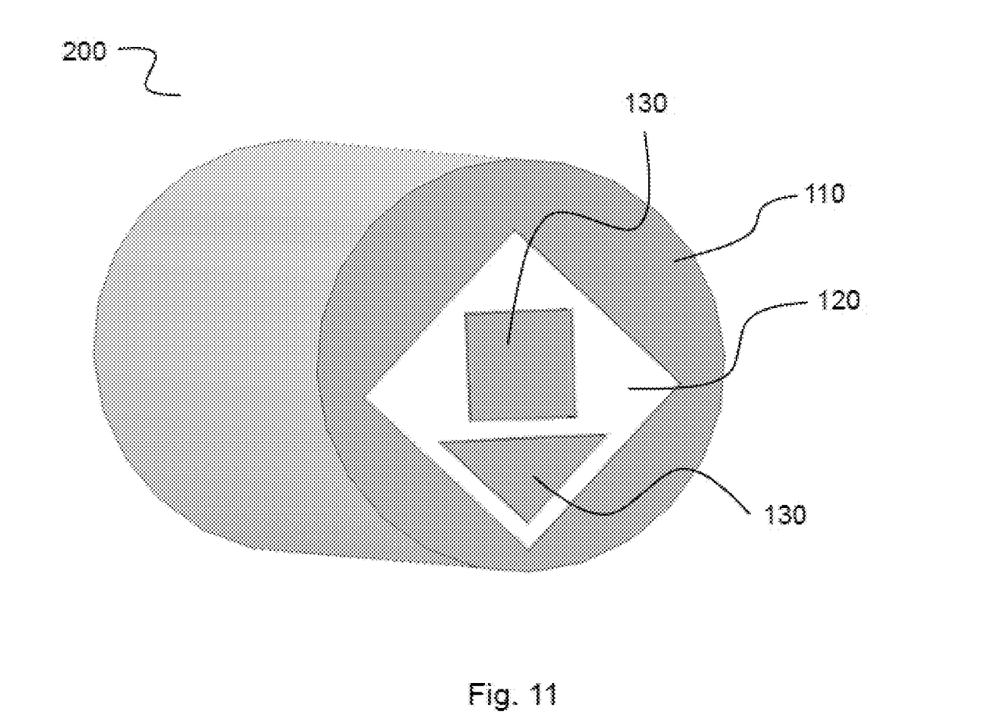
FIG. 11 illustrates a composite precursor according to Example 1.

FIG. 11 illustrates a corresponding drawing of the composite precursor according to this example, assembled from the monolithic metal precursor according to FIG. 10, the sacrificial outer element 110 and two sacrificial core elements 130, wherein the sacrificial core elements have been inserted into the two cavities B 121 of the monolithic metal precursor. The sacrificial core elements were made of nickel, respectively.

Although specific embodiments have been illustrated and described herein, it will be appreciated by those of ordinary skill in the art that a variety of alternate and/or equivalent implementations may be substituted for the specific embodiments illustrated and described without departing from the scope of the present embodiment. This application is intended to cover any adaptations or variations of the specific embodiments discussed herein. Therefore, it is intended that this embodiment be limited only by the claims and the equivalents thereof

TABLE 1

Dimensions of composite precursor and formed composite according to Example 1.

| Dimension | Composite precursor | Formed composite | Shrink factor |
|---|---|---|---|
| Outer diameter | 14.500 mm | 1.740 mm | 8.33/1 |
| Side length rectangular PtIr 10 | 7.910 mm | 0.952 mm | 8.31/1 |
| Side length rectangular PtIr 11 | 7.900 mm | 0.958 mm | 8.25/1 |
| Side length rectangular Ni | 3.780 mm | 0.458 mm | 8.25/1 |
| Side length rectangular Ni | 3.780 mm | 0.458 mm | 8.25/1 |
| Hypotenusis triangular Ni | 5.870 mm | 0.710 mm | 8.26/1 |
| Side length triangular Ni | 4.150 mm | 0.504 mm | 8.23/1 |
| Side length triangular Ni | 4.150 mm | 0.504 mm | 8.23/1 |
| Distance rectangular Ni to triangular Ni | 0.625 mm | 0.075 mm | 8.37/1 |
| Distance triangular Ni to rectangular PtIr10 | 0.625 mm | 0.075 mm | 8.37/1 |
| Distance triangular Ni to rectangular PtIr11 | 0.625 mm | 0.075 mm | 8.37/1 |
| Min factor | | | 8.23/1 |
| Max factor | | | 8.37/1 |
| Mean factor | | | 8.29/1 |

The invention claimed is:

1. A process for preparing a shaped metal product for a medical device, wherein the process comprises:
   1) Providing a sacrificial outer element comprising a cavity A;
   2) Providing a monolithic metal precursor comprising a cavity B;
   3) Providing a sacrificial core element;
   4) Preparing a composite precursor by inserting the monolithic metal precursor into cavity A of the sacrificial outer element, and by inserting the sacrificial core element into cavity B of the monolithic metal precursor;
   5) Forming the composite precursor obtained in 4) to obtain a formed composite having a smaller outer diameter than the diameter of the composite precursor obtained in 4);
   6) Separating a composite disk from the formed precursor obtained in 5);
   7) Removing the sacrificial outer element and the sacrificial core element from the composite disk obtained in 6).

2. The process according to claim 1, wherein the outer shape of the monolithic metal precursor, as seen in a radial cross section, has an open or a closed outer shape.

3. The process according to claim 2, wherein said closed outer shape is a shape selected from the list consisting of oval, polygonal, cubic, rectangular, and circular.

4. The process according to claim 2, wherein said open outer shape is a shape selected from the list consisting of U-shaped, L-shaped, S-shaped or H-shaped.

5. The process according to claim 1, wherein the inner shape of the monolithic metal precursor, as seen in a radial cross section, is a non-circular shape.

6. The process according to claim 1, wherein the sacrificial outer element and the sacrificial core element together form a monolithic metal element.

7. The process according to claim 1, wherein the monolithic metal precursor is prepared by at least one process selected from the group of electrical discharging machining, additive manufacturing, deep-hole drilling and milling.

8. The process according to claim 1, wherein the monolithic metal precursor comprises a metal selected from the group consisting of platinum, gold, iridium, steel, titanium, hafnium, niobium, tantalum, cobalt, nickel, chromium, zirconium, rhenium, tungsten, molybdenum, and alloys of any one of these metals, selected from the group consisting of nickel cobalt alloy, steel, platinum and platinum iridium alloy.

9. The process according to claim 1, wherein 5) comprises a drawing process, wherein said drawing process is carried out with a deformation factor of between 5 and 40%, per individual drawing, or with a die cast having a total included angle 2 $\alpha$ in the range of from 5 to 20°.

10. The process according to claim 1, wherein 5) comprises a drawing process, wherein said drawing process is carried out with a deformation factor of between 15 and 30%, per individual drawing, or with a die cast having a total included angle 2 $\alpha$ in the range of from 5 to 15°.

11. The process according to claim 9, wherein the composite precursor is annealed between individual drawing steps of said drawing process.

12. The process according to claim 1, wherein 5) comprises an extrusion process.

13. The process according to claim 1, wherein the monolithic metal precursor is formed in 5) to adopt a smaller dimension without substantially changing its overall geometry.

\* \* \* \* \*